(12) United States Patent
Matsuura

(10) Patent No.: US 7,201,717 B2
(45) Date of Patent: Apr. 10, 2007

(54) ELECTRONIC ENDOSCOPE

(75) Inventor: Nobuyuki Matsuura, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/167,324

(22) Filed: Jun. 11, 2002

(65) Prior Publication Data

US 2002/0193663 A1    Dec. 19, 2002

(30) Foreign Application Priority Data

Jun. 13, 2001    (JP)    ............................. 2001-178909

(51) Int. Cl.
*A61B 1/05* (2006.01)
(52) U.S. Cl. ...................... 600/129; 600/130; 600/109; 600/110
(58) Field of Classification Search ................ 600/129, 600/130, 109, 110, 141; 348/76
See application file for complete search history.

(56) References Cited

U.S. PATENT DOCUMENTS

| | | | | |
|---|---|---|---|---|
| 4,646,721 A | * | 3/1987 | Arakawa | ..................... 600/130 |
| 4,745,470 A | * | 5/1988 | Yabe et al. | .................... 348/76 |
| 4,809,680 A | * | 3/1989 | Yabe | ........................... 600/130 |
| 4,832,003 A | * | 5/1989 | Yabe | ........................... 600/109 |
| 4,918,521 A | * | 4/1990 | Yabe et al. | .................... 348/76 |
| 5,050,584 A | * | 9/1991 | Matsuura | ..................... 600/130 |
| 5,411,020 A | | 5/1995 | Ito | |
| 5,456,245 A | * | 10/1995 | Bornhop et al. | ............ 600/139 |

FOREIGN PATENT DOCUMENTS

| | | |
|---|---|---|
| JP | 4-358114 | 12/1992 |
| JP | 5-211999 | 8/1993 |
| JP | 8-152565 | 6/1996 |

OTHER PUBLICATIONS

Translation of Ogyu (Unexamined Jap. Pat. 05-211999.*

* cited by examiner

*Primary Examiner*—John P. Leubecker
(74) *Attorney, Agent, or Firm*—Scully, Scott, Murphy & Presser, P.C.

(57) ABSTRACT

A hard distal component formed at the distal part of an inserting section and a leading bending piece included in a bending section are joined using a substantially cylindrical hard joint pipe. Build-in components including an imaging device that is a CCD are placed in the joint pipe. An adhesive is poured into the surroundings of the built-in components in the joint pipe, whereby the built-in components are locked. Thus, the structure of the distal component is simplified and the surroundings thereof are made thinner.

7 Claims, 5 Drawing Sheets

ELECTRONIC ENDOSCOPE

This application claims benefit of Japanese Application No. 2001-178909 filed on Jun. 13, 2001, the contents of which are incorporated by this reference.

BACKGROUND OF THE INVENTION

Field of the Invention and Description of the Related Art

The present invention relates to an electronic endoscope having an imaging unit placed in a distal component included therein.

In recent years, endoscopes have been widely adopted in the fields of medicine and industries alike.

Moreover, an electronic endoscope having an imaging unit incorporated in the distal part of an inserting section thereof has prevailed widely.

Compared with an optical endoscope, the electronic endoscope has the merit that an operator can view endoscopic images displayed on a monitor but may not observe an object with naked eyes through an eyepiece unit, and can record or reproduce images easily.

Talking of the structure of the distal component formed as the distal part of the inserting section of the electronic endoscope, as disclosed in, for example, Japanese Unexamined Patent Application Publication No. 8-152565, a solid-state imaging device, a circuit card, and others are placed in a substantially pipe-like protective support member (for example, a component 5 shown in FIG. 5 in the publication). The support member is then locked in the distal component.

In the foregoing structure of the distal component employed in the related art, the support member is, as mentioned above, used to protect the solid-state imaging device and circuit card, and locked in the distal component. A space large enough to store and lock the support member must therefore be preserved in the distal component. It is therefore hard to design the whole of the distal component thinly.

OBJECTS AND SUMMARY OF THE INVENTION

Accordingly, an object of the present invention is to provide an electronic endoscope making it possible to reduce the outer diameters of the surroundings of a distal component.

Another object of the present invention is to provide an electronic endoscope whose cost can be lowered.

According to the present invention, an electronic endoscope consists mainly of an inserting section, a hard distal component, a bending section, a joint pipe, built-in components, and a filler. The inserting section is elongated and flexible. The distal component is formed at the distal part of the inserting section. The bending section is proximal to the distal component and has a plurality of bending pieces concatenated so that the pieces can rotate freely. The joint pipe has the distal part thereof fixed to the periphery of the distal component and has the rear part thereof coupled to the leading bending piece included in the bending section. The built-in components include an imaging device that is placed in the joint pipe. The filler is applied to the surroundings of the built-in components in order to lock the built-in components in the joint pipe. Herein, the built-in components including the imaging device are placed in the joint pipe that joins the distal component and the leading bending piece, and then locked firmly. The structure of the distal component is thus simplified, and the surroundings of the distal component can be designed thinly.

BRIEF DESCRIPTION OF THE DRAWINGS

FIG. 1 schematically shows the configuration of an electronic endoscope system including an electronic endoscope in accordance with the first embodiment;

FIG. 2 is a longitudinal sectional view showing the structure of the distal part of an inserting section of the electronic endoscope;

FIG. 3 is a schematic front view of the distal end of the inserting section of the endoscope with an imaging unit, a forceps channel, an aeration/perfusion channel, and a light guide fiber bundle arranged properly;

FIG. 4 is a schematic front view of the distal end of the inserting section of the endoscope with the imaging unit, forceps channel, aeration/perfusion channel, and light guide fiber bundle arranged properly;

FIG. 5 is a schematic front view of the distal end of the inserting section of the endoscope with the imaging unit, forceps channel, aeration/perfusion channel, and light guide fiber bundle arranged properly;

FIG. 6 is a schematic front view of the distal end of the inserting section of the endoscope with the imaging unit, forceps channel, aeration/perfusion channel, and light guide fiber bundle arranged properly;

FIG. 7 is a longitudinal sectional view showing the structure of the distal part of an inserting section of a variant;

FIG. 8 is a longitudinal sectional view showing the structure of the distal part of an inserting section of an electronic endoscope in accordance with the second embodiment; and FIG. 9 is a longitudinal sectional view showing the structure of the distal part of an inserting section of a variant.

DETAILED DESCRIPTION OF THE PREFERRED EMBODIMENTS

Referring to FIG. 1 to FIG. 7, the first embodiment of the present invention will be described below.

Figure 1:
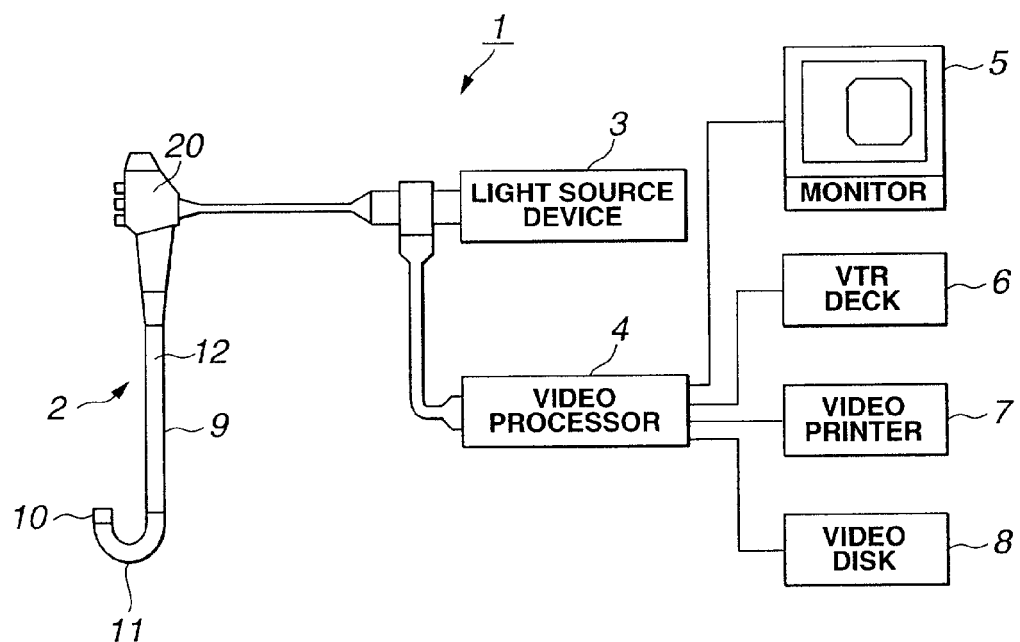
FIG. 1 to FIG. 7 are concerned with a first embodiment of the present invention.

As shown in FIG. 1, an electronic endoscope system 1 consists mainly of an electronic endoscope 2, a light source device 3, a video processor 4, a monitor 5, a videotape recording (VTR) deck 6, a video printer 7, and a videodisk 8. The electronic endoscope 2 has an inserting section 9 that is thin and flexible, and an operation unit 20 coupled to the rear end of the inserting section 9. The light source device 3 is connected to the electronic endoscope 2 via a connector fixed to the end of a universal cord that extends laterally from the operation unit 20 of the electronic endoscope 2, and supplies illumination light to the electronic endoscope 2. The video processor 4 is also connected to the electronic endoscope with the connector, and processes signals produced by an imaging means incorporated in the electronic endoscope 2. Endoscopic images are displayed on the monitor 5. The VTR deck 6 records a video signal. The video printer 7 prints endoscopic images. The videodisk 8 is a disc-like recording medium on which a video signal is recorded. The monitor 5, VTR deck 6, video printer 7, and videodisk 8 are connected to the video processor 4 through video signal output terminals of the video processor 4.

The inserting section 9 has a hard distal component 10, a freely bendable bending section 11, and a flexible tube 12, which has flexibility, coupled to one another in that order from the distal end thereof. An angling knob that is not shown and formed on the operation unit 20 is turned, whereby the bending section 11 can be bent in a desired direction. By bending the bending section 11, the distal component 10 immediately succeeding the bending section can be angled in a direction permitting a user to observe an object easily, or the distal component 10 can be inserted smoothly along a tortuous lumen.

The light source device 3 has a light-emitting source with which an object is illuminated. Illumination light emanating from the light-emitting source is propagated over the universal cord, the operation unit 20, and the light guide fiber bundle 21 running through the inserting section 9 (see FIG. 2). The illumination light is then radiated from the distal end of the light guide fiber bundle 21, which is locked in the distal component 10 of the inserting section 9, towards an object through an illumination window.

The video processor 4 performs various kinds of signal processing on an image signal that represents an object and that has undergone photoelectric conversion in the imaging unit 22 (see FIG. 2) which will be described later. An object image represented by a video signal resulting from the signal processing is displayed on the monitor 5. If necessary, the video signal is transferred to the VTR deck 6 that records or reproduces the video signal, the video printer 7 that prints the object image according to the video signal, and the videodisk 8 that is a large-capacity storage device on which the video signal is recorded.

Figure 2:
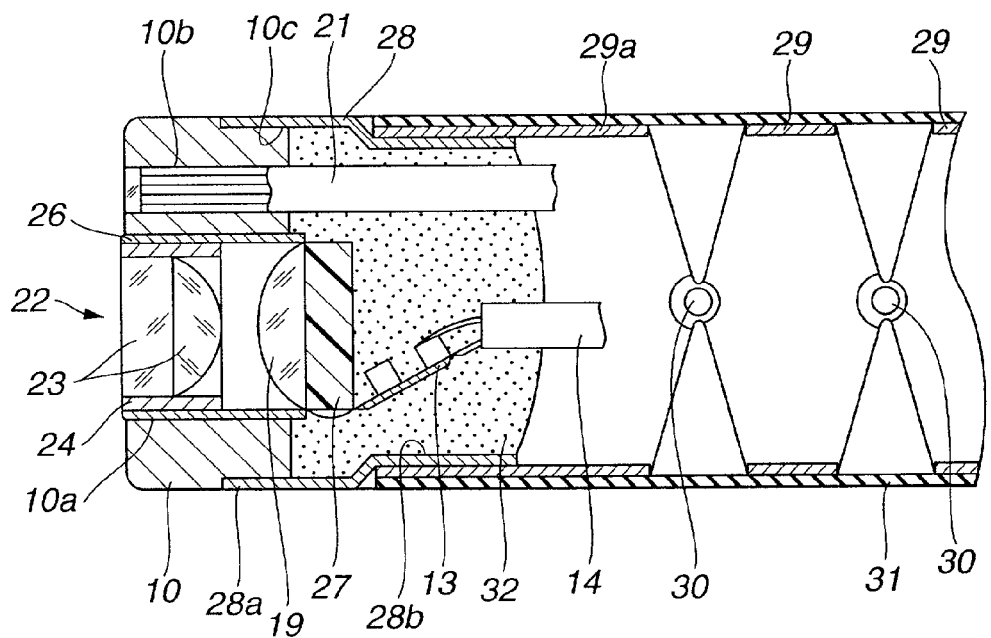
Figure 3:
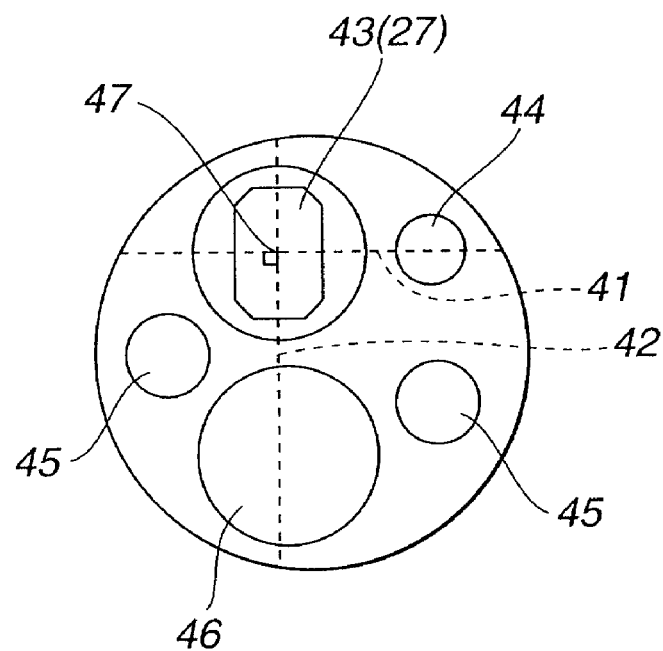
Figure 4:
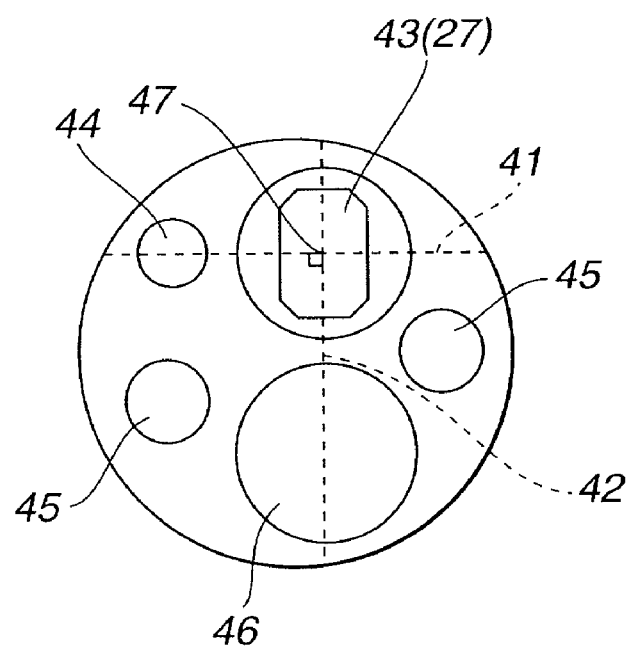
Figure 5:
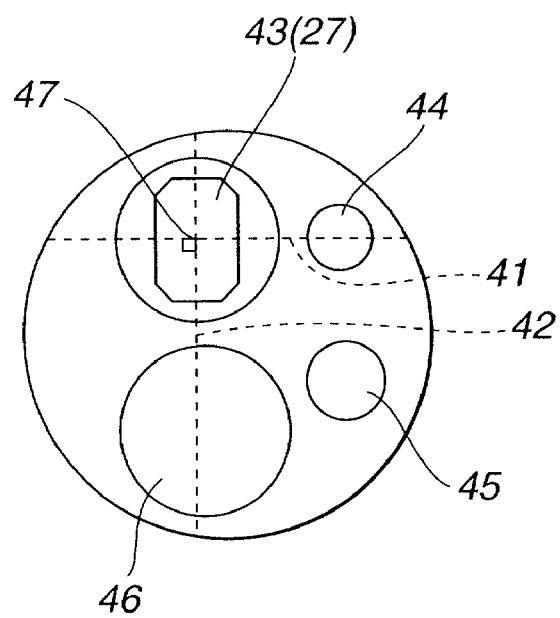
Figure 6:
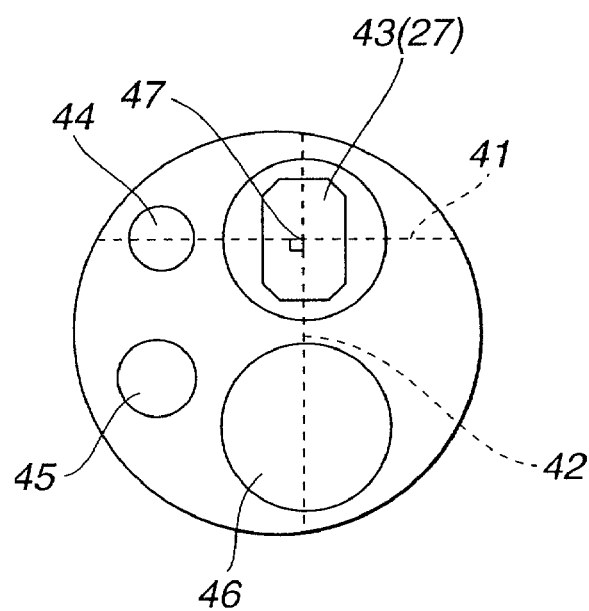
Figure 7:
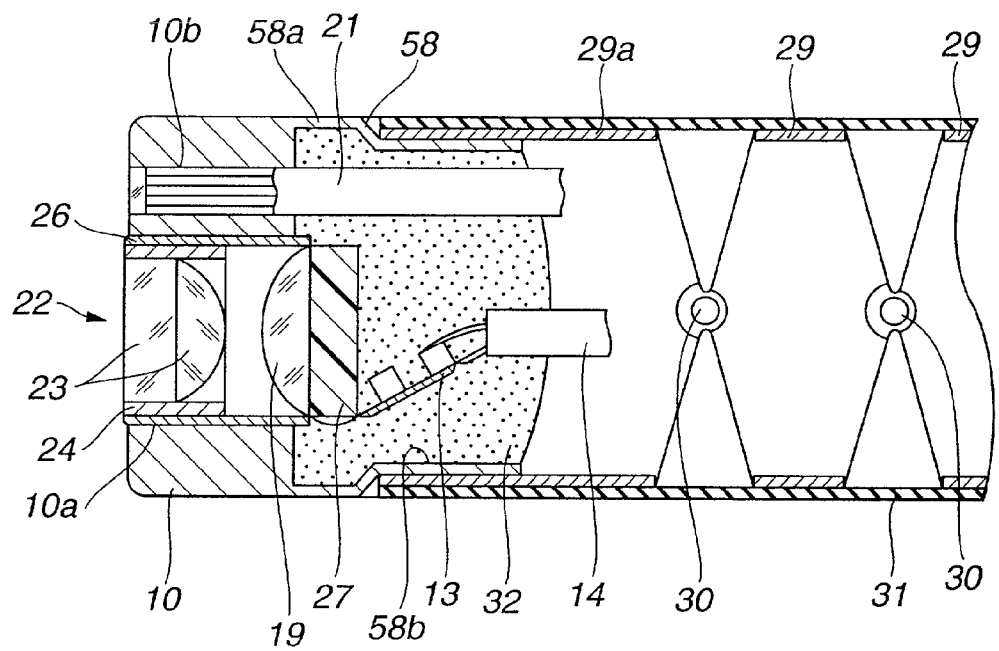

FIG. 2 is a sectional view showing the surroundings of the distal component 10 that is formed at the distal part of the inserting section 9.

The distal component 10 is shaped like a substantially short column using a metallic hard member. An imaging unit placement hole 10a is bored by axially piercing the central lower part of the distal component 10. A light guide placement hole 10b is bored above the imaging unit placement hole 10a by axially piercing the upper part of the distal component 10. An aeration/perfusion tube placement hole (not shown) and a forceps channel (not shown) through which a treatment appliance such as forceps are inserted are also bored by axially piercing the upper part of the distal component 10.

The rear periphery of the distal component 10 has a joint portion 10c formed as a carved steplike portion. A large-diameter portion 28a that is the distal part of the joint pipe 28 having a large diameter is engaged with and fixed to the joint portion 10c. The joint pipe 28 is formed with a stainless steel pipe or any other hard joint pipe.

In this case, the distal component 10 has the rear part of the periphery thereof carved by the thickness of the joint pipe 28, thus forming the joint portion 10c. The large-diameter portion 28a that is the distal part of the joint pipe 28 is engaged with the joint portion 10c and secured by performing brazing or the like. Therefore, the distal part of the joint pipe 28 has the same outer diameter as the distal component 10.

As mentioned above, the joint pipe 28 fills the role of joining the distal component 10 and the bending section 11 disposed at the rear end of the distal component 10. The first half of the joint pipe 28 is formed as the large-diameter portion 28a that has the same diameter as the first half of the distal component 10. The second half of the joint pipe 28 is formed as a smaller-diameter portion 28b that is a steplike or tapered portion whose outer diameter is smaller than the outer diameter of the first half thereof. The smaller-diameter portion 28b is engaged with and fixed to the internal surface of the distal part of the leading bending piece 29a included in the bending section 11.

The bending section 11 has the plurality of bending pieces 29, which are formed with substantially annular short tubular bodies, combined with one another using rivets 30, which are caulked or the like, so that the bending pieces can rotate freely. The plurality of bending pieces 29 is disposed axially in the inserting section. The periphery of the bending section 11 is sheathed with an armor 31 made of a bendable rubber or the like. The outer diameter of the first half of the distal component 10, the outer diameter of the first half of the joint pipe 28, and the outer diameter of the armor 31 are the same.

In other words, the outer diameter of the smaller-diameter portion 28b is smaller than the outer diameter of the large-diameter portion 28a by the sum of the thickness of the leading bending piece 29a and the thickness of the armor 31. The periphery of the smaller-diameter portion 28b is covered with the leading bending piece 29a and armor 31.

The imaging unit 22 is placed in the imaging unit placement hole 10a. The imaging unit 22 consists mainly of a stationary drum 26 and a charge-coupled device (CCD) 27. The stationary drum 26 bears a lens frame 24 that holds an objective optical system 23 composed of objectives, and a field lens 19 which is located behind the objective optical system 23 with the optical axis thereof aligned with the optical axis of the objective optical system 23. The CCD 27 is a solid-state imaging device and located at the position of the image plane corresponding to the back surface of the field lens 19. The stationary drum 26 is fitted and locked in the imaging unit placement hole 10a, and thus disposed in the distal component 10.

A circuit card 13 or the like on which electronic parts including ICs and capacitors are mounted is connected to the CCD 27 included in the imaging unit 22. The tip of a signal cable 14 passed through the inserting section 9 is coupled to the circuit card 13. Consequently, the distal parts of the CCD 27, circuit card 13, and signal cable 14 are disposed in the joint pipe 28.

Moreover, the distal part of the light guide fiber bundle 21 lying through the inserting section 9 is fitted and locked in the light guide placement hole 10b in the distal component 10. Illumination light is radiated from the distal end of the fiber bundle 21 towards an object through the illumination window. Therefore, the portion of the light guide fiber bundle 21 adjoining the distal component 10 and extending backward from the distal component 10 is also disposed in the joint pipe 28.

An adhesive 32 is then poured into the joint pipe 28. By filling the joint pipe 28 with the adhesive 32, the built-in components disposed in the joint pipe 28 are integrated into and locked in the joint pipe 28. The built-in components include the CCD 27, the circuit card 13, the distal part of the signal cable 14, the substantially distal part of the light guide fiber bundle 21, and the substantially distal parts of the aeration/perfusion tube and channel tube that are not shown.

As mentioned above, the CCD 27 disposed in the joint pipe 28 and its surroundings are locked using the adhesive 32. This results in greater strength than strength attained using the joint pipe 28 alone. The distal component is thus reinforced. Moreover, since the CCD 27 and its surroundings are locked using the adhesive 32, even if cleaning is performed at every completion of an endoscopic examination, the adverse effect of moisture on the CCD 27 and other electronic parts can be alleviated.

As shown in FIG. 2, in the joint pipe 28 projecting backward from the distal component 10, in addition to the built-in components including the CCD 27, the distal part of the flexible signal cable 14, the distal part of the flexible light guide fiber bundle 21, and their surroundings are locked with the adhesive 32 applied thereto. This results in a hard assembly. The rear end of the hard assembly is located forward beyond the distal part of the bendable bending section 11, that is, the rivet 30 fixed to the rear end of the leading bending piece 29a. Consequently, it is suppressed that when the bending section 11 is bent, large force is applied to the flexible members including the flexible signal cable 14.

The present embodiment has been described on the assumption that the distal component 10 and joint pipe 28 are separated from each other. The present invention is not limited to the distal component 10 and joint pipe 28 that are separated from each other. Like a variant shown in FIG. 7, a tubular body 58 (equivalent to the joint pipe 28) may be integrated with and extended from the rear end of the distal component 10.

In this case, the distal part of the tubular body 58 is formed as a large-diameter portion 58a. The diameter of the tubular body 58 gets smaller stepwise at the middle thereof, whereby the proximal part of the tubular body 58 is formed as a smaller-diameter portion 58b. The leading bending piece 29a is engaged with and fixed to the smaller-diameter portion 58b.

FIG. 3 to FIG. 6 show examples of proper arrangement of the imaging unit 43, forceps channel 46, aeration/perfusion channel 44, and light guide fiber bundle 45 in the distal part of the endoscope.

In FIG. 3 to FIG. 6, a dashed line 41 indicates horizontal directions (directions determined with opposite sides) along a line passing through a center 47 of (the substantially rectangular CCD 27 included in) the imaging unit 43. The center of the aeration/perfusion channel 44 lies substantially on the dashed line 41.

In other words, the aeration/perfusion channel 44 through which air or water is fed in order to clean the periphery of the objective optical system 23 is disposed so that the center thereof will lie on the dashed line 41. The dashed line 41 passes through the center of the substantially rectangular CCD 27 and runs parallel to the horizontal opposite sides of the CCD 27. The dashed line 41 extends perpendicularly to the vertical opposite sides of the substantially rectangular CCD 27.

A dashed line 42 is a line linking the center 47 of the imaging unit 43 and the center of the forceps channel 46. The dashed line 42 is orthogonal to the dashed line 41. Namely, the forceps channel 46 is located immediately below a field of view offered by the endoscope.

With the components arranged as mentioned above, the aeration/perfusion channel 44 is located in one of the directions determined with the opposite sides of the imaging unit 43 (normally, an angle of visibility is narrower in the directions determined with the opposite sides of a rectangle than in the directions determined with the diagonals thereof). Therefore, a nozzle attached to the distal end of the aeration/perfusion channel (in FIG. 3 and FIG. 5, the nozzle is supposed to lie by the right side of the imaging unit 43 when seen from the distal end of the endoscope in, while in FIG. 4 and FIG. 6, the nozzle is supposed to lie by the left side thereof when seen from the distal end thereof) will not enter the field of view offered by the endoscope. Moreover, since the forceps channel 46 is located immediately below the imaging unit 3, a treatment appliance can be moved to an object to be treated by angling the endoscope solely vertically. For treatment, the endoscope can be manipulated easily.

As described above, according to the present embodiment, the distal component 10 and the leading bending piece 29a in the bending section 11 are joined using the joint pipe 28. The adhesive 32 is poured into the joint pipe 28, whereby the built-in components placed or inserted in the joint pipe 28 are locked in and integrated into the joint pipe 28. Unlike the related art, it is unnecessary to preserve the space, in which the support member of the imaging unit is locked, within the distal component. Moreover, while the surroundings of the CCD whose strengths are usually insufficient can be made strong enough, the outer diameters of the surroundings of the distal component 10 can be made smaller.

Since the space is unnecessary, the surroundings of the distal component 10 can be designed compactly. Specifically, as shown in FIG. 2, an inserting section is designed thinly with the outer diameter of the first half of the distal component 10, the outer diameter of the first half of the joint pipe 28, and the outer diameter of the armor 31 made the same. This results in an endoscope thinner than the endoscope in accordance with the related art. Moreover, according to the present embodiment, the structure of an endoscope can be made simpler than that of the endoscope in accordance with the related art, and the cost thereof can be made lower.

Next, the second embodiment of the present invention will be described with reference to FIG. 8.

According to the first embodiment, the diameter of the axially rear part of the joint pipe 28 is smaller than that of the axially distal part thereof by the sum of the thickness of the leading bending piece 29a and the thickness of the armor 31. In other words, the joint pipe 28 has the outer diameter thereof varied axially. According to the second embodiment, as shown in FIG. 8, a hard joint pipe 28' has the outer diameter thereof made equal to the outer diameter of the large-diameter portion 28a shown in FIG. 2 over the whole length thereof, and is shaped annularly.

The distal part of the joint pipe 28' is, similarly to the counterpart included in the first embodiment, fixed to the distal component 10. According to the present embodiment, however, the joint pipe 28' is engaged with and fixed to the leading bending piece 29a that is axially longer than the leading bending piece 29a included in the first embodiment.

As mentioned above, according to the present embodiment, the leading bending piece 29a is made axially longer. For example, the leading bending piece 29a is extended forward until the distal end thereof abuts on the rear end of the distal component 10. The leading bending piece 29a is then coupled and fixed to a joint pipe 28', which is engaged with and abutted on the periphery of the distal component 10, by performing brazing or the like.

According to the present embodiment, the joint pipe 28' can be designed to be simpler than the joint pipe 28 included in the first embodiment. This results in a reduction of the cost of an endoscope.

Moreover, in this case, the smaller-diameter portion 28b that is engaged with the internal surface of the leading bending piece 29a is not needed in order to couple and fix the joint pipe 28' to the leading bending piece 29a. The large-diameter portion 28a alone is needed. Therefore, the storage space in which the built-in components including the CCD 27 are stored can be preserved widely. In other words, the hard distal part or the distal component 10 can be designed thinly.

Figure 8:
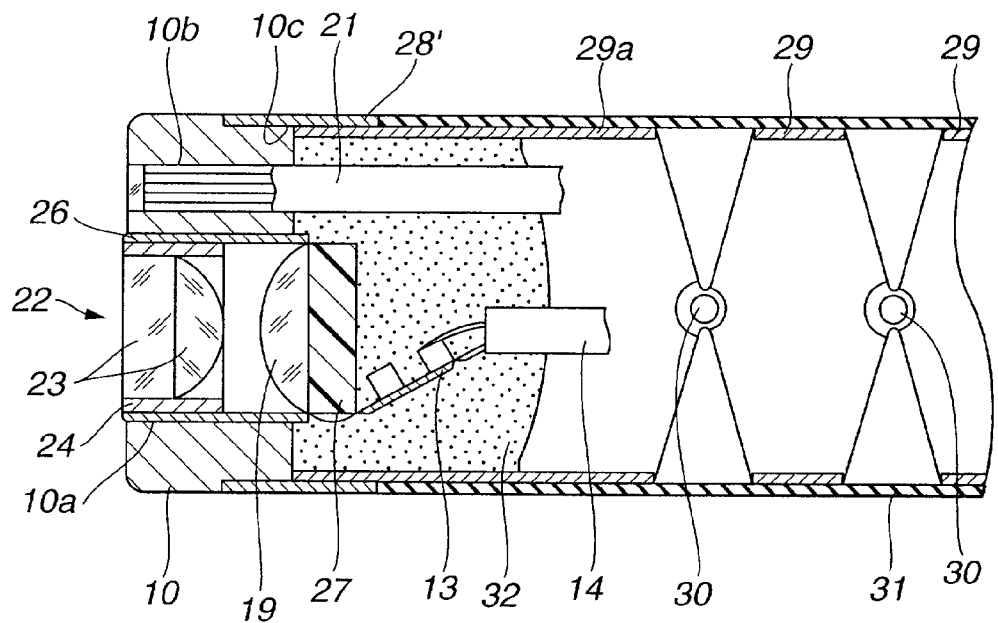
FIG. 8 and FIG. 9 are concerned with a second embodiment of the present invention.
Figure 9:
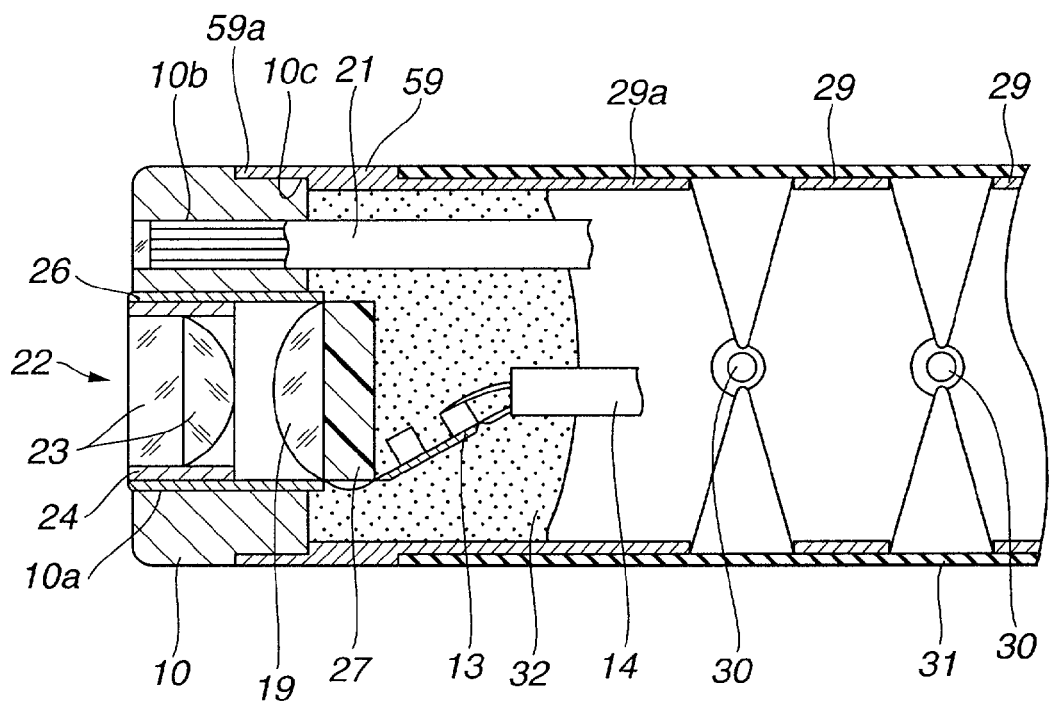

FIG. 9 shows the structure of the distal part of an inserting section of a variant. In the structure shown in FIG. 8, the joint pipe 28' and leading bending piece 29a are separated from each other. In the structure employed in the variant, as shown in FIG. 9, the joint pipe and leading bending piece are integrated with each other.

Specifically, a joint pipe portion 59 is formed as a steplike distal part of the leading bending piece 29a using the same member. The distal part 59a of the joint pipe portion 59 is fixed to the distal component 10. The other components are identical to those shown in FIG. 8.

The advantages provided by the variant are nearly the same as those provided by the second embodiment shown in FIG. 8.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electronic endoscope comprising:

an elongated and flexible inserting section;

a hard distal component formed at the distal part of the insertion section;

a bending section proximal to the distal component and having a plurality of bending pieces concatenated so that the bending pieces can rotate freely by a plurality of rotatable concatenating portions, respectively;

a joint pipe having the distal part thereof fixed to the outer periphery of the distal component and having the rear part thereof fixed to the inner periphery of a leading bending piece included in the bending section, so as to concatenate the distal component and the leading bending piece, the joint pipe being formed of a cylindrical-shaped hard member placed toward the distal part from a leading rotatable concatenating portion of the leading bending piece;

built-in components placed in the joint pipe and including at least a circuit substrate connected to an imaging device and a signal cable connected to the circuit substrate; and a filler sealingly poured into a space formed between the inner surface of the joint pipe and the surroundings of the built-in components inclusive of the connecting portion of at least the circuit substrate and the signal cable of the built-in components, the filler hardening after pouring into the space thereby to lock in the joint pipe, the connecting portion of the circuit substrate and the signal cable placed in the joint pipe, and the filler being formed of a material differing from that of the hard member.

2. The electronic endoscope according to claim 1, wherein said built-in components further include at least one of an aeration/perfusion tube, a channel tube and a light guide fiber bundle, which is locked in the joint pipe together with the connection portion of the circuit substrate and the signal cable.

3. The electronic endoscope according to claim 1, wherein the circuit substrate has electronic parts mounted thereon for driving the imaging device.

4. An electronic endoscope according to claim 1, wherein the distal part of said joint pipe is fixed to said distal component, while the rear part thereof is fixed to said leading bending piece and has a smaller diameter.

5. An electronic endoscope according to claim 1, wherein the diameter of the rear part of said joint pipe is smaller than that of the distal part thereof by the sum of the thickness of said leading bending piece and the thickness of an armor sheathing said plurality of bending pieces.

6. An electronic endoscope according to claim 1, wherein said joint pipe has an annular shape with the outer diameter thereof held axially unchanged.

7. An electronic endoscope according to claim 1, wherein said filler is an adhesive.

* * * * *